United States Patent
Platzek et al.

[11] Patent Number: 6,156,890
[45] Date of Patent: Dec. 5, 2000

[54] PROCESS FOR THE PRODUCTION OF CYCLENE

[75] Inventors: Johannes Platzek; Karsten Hoyer; Klaus-Dieter Graske; Bernd Raduechel, all of Berlin, Germany

[73] Assignee: Schering Aktiengesellschaft, Berlin, Germany

[21] Appl. No.: 09/451,702

[22] Filed: Dec. 1, 1999

Related U.S. Application Data

[60] Provisional application No. 60/116,230, Jan. 15, 1999.

[51] Int. Cl.[7] .................................................. C07D 255/02
[52] U.S. Cl. ............................................................ 540/474
[58] Field of Search ............................................. 540/474

[56] References Cited

U.S. PATENT DOCUMENTS

| | | | |
|---|---|---|---|
| 5,434,262 | 7/1995 | Guilard et al. | 540/474 |
| 5,589,595 | 12/1996 | Sandnes et al. | 540/474 |
| 5,880,281 | 3/1999 | Argese et al. | 540/474 |
| 5,886,174 | 3/1999 | Ripa et al. | 540/474 |
| 6,013,793 | 1/2000 | Argese et al. | 540/474 |

FOREIGN PATENT DOCUMENTS

| | | |
|---|---|---|
| 9628432 | 9/1996 | WIPO . |
| 9749691 | 12/1997 | WIPO . |
| 9849151 | 11/1998 | WIPO . |

OTHER PUBLICATIONS

Herve G. et al : "condensation of glyoxal with triethylenetramine. Steriochemistry, cyclization and deprotection." TETRAHEDRON LETTERS., Bd 40 ,Nr.13,26 Mar. 1999.
Chemical Abstracts, vol. 131, No.17, 25 Oct. 1999; abstract No. 228667, MO Z. et al: "Recent developments in the synthesis of 1,4,7,10–tetraazacyclododecane" & HUAXUESHIJI Bd.21 Nr.4, 1999, pp. 218–219.

*Primary Examiner*—Deborah C. Lambkin
*Attorney, Agent, or Firm*—Millen, White, Zelano & Branigan, P.C.

[57] ABSTRACT

A new single-pot process for the production of cyclene is described.

19 Claims, No Drawings

PROCESS FOR THE PRODUCTION OF CYCLENE

This application claims the benefit of U.S. Provisional application Ser. No. 60/116,230, filed Jan. 15, 1999.

The invention relates to the subject that is characterized in the claims, i.e., a new process for the production of cyclene.

Cyclene (1,4,7,10-tetraazacyclododecane) is a frequently used starting material in the production of macrocyclic complexing agents and is mainly used in the area of nuclear resonance tomography as a ligand for gadolinium. Two preparations are already commercially available with Pro-Hance® of Bristol-Myers-Squibb and Dotarem® of Guerbet. Special research and development projects also use cyclene as a starting material. There is therefore a need for an easy and economical process for the production of this educt.

One of the first published processes (Richman and Atkins, J. Am. Chem. Soc. 1974, 96, p. 2268) employs the cyclization of a sodium bis-sulfonamide with a corresponding functionalized diethylene sulfonamide. In their synthesis, Weisman and Reed (J. Org. Chem. 1996, 61, pp. 5186–5187) use the reaction of a bis-thioimidoester with triethylenetetramine for the creation of a tricyclic bis-imine, which is ultimately hydrolyzed to cyclene after reduction.

The processes of V. Panetta et al. (Tetrahedron Lett. 1992, Vol. 33, No. 38, pp. 5505–5508), which perform a cyclization of a tetra-trifluoromethanesulfonic acid amide of triethylenetetramine with 1,2-dibromoethane, follow a more indirect approach to cyclene. The last reaction step comprises the release of cyclene. The process of the Nycomed Company (WO 96/28433) after the production of tribenzyl-cyclene is also dependent on such a procedure. The synthesis is accomplished by the reaction of a suitable triamine with a monoamine or the two suitable diamines. The process that is disclosed in DE 19608307 and that contains a tetramerization of N-benzylaziridine as a key step also results in tetrabenzylcyclene.

As described in WO 97/31005 and U.S. Pat. No. 5,587,451, the Dow Chemical Company uses a bis-imidazoline that starts from triethylenetetramine as an intermediate product. The rings in the tetracyclic intermediate product are closed with 1,2-dibromoethane. The subsequent hydrolysis releases the cyclene.

As described in WO 97/49691, the Bracco Company uses a direct approach to cyclene, which starts with the condensation of triethylenetetramine with glyoxal—which was already disclosed by Weisman et al. (Tetrahedron Lett. 1980, Vol. 21, pp. 335–338). Then, the latter is converted into a tetracyclic intermediate compound by reaction with 1,2-dibromoethane. The removal of the ethylene bridge that connects the four heteroatoms is carried out by oxidation with bromine with subsequent hydrolysis or also by hydrolysis with a primary diamine (WO 98/49151). The total yield is indicated with 25%.

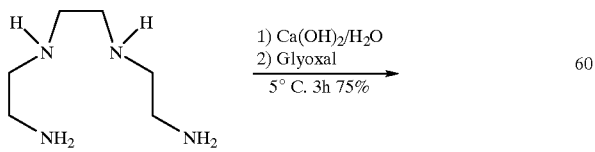

Diagram 1: Synthesis Sequence of the Bracco Company (WO 97/49691)

The synthesis that is disclosed in WO 96/28432 of the Nycomed Company resembles the above-described synthesis, with the decisive difference being the hydrolysis of the central ethylene bridge. Here, the reaction is achieved by addition of hydroxylamine in an ethanolic solution while being heated. The total yield for this reaction sequence is approximately 45%.

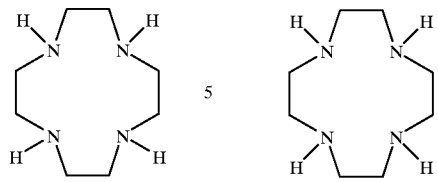

Diagram 2: Synthesis Sequence of the Nycomed Company (WO 96/28432)
Evaluation of the Process:

The process according to WO 97/49691, supported by empirical reworking, has some decisive drawbacks, which are summarized briefly below:

The production of the tricyclic compound cannot be reproduced as described, since:

The calcium hydroxide cannot be quantitatively separated.

Larger amounts of water must be distilled off.

The product does not accumulate as an oil, as indicated. The purification of the tetracyclic compound is very expensive:

The extraction of the product from a solid reduces the yield.

Hydrolysis into cyclene has proven to be very difficult:

An autoclave reaction must be performed at pH=14 and at 185° C.

The product crystallizes poorly and with heavy contamination from the reaction solution.

The process according to WO 96/28432 also gives rise to criticism. The basic drawbacks are listed below:

All synthesis stages have long stirring times.

The purification of the tetracyclic compound is carried out via a preparative column chromatography.

The hydrolysis to cyclene lasts for a very long time, and the indicated purification method does not yield the product in the desired purity.

All other processes comprise multistage synthesis sequences, in which intermediate products are isolated, which generally is time-consuming and raw material-intensive. The process of Weismann and Reed is ruled out for commercial synthesis, since it is dependent on dithiooxamide (about DM 400/100 g) as one of the starting materials. In the process of Richman and Atkins as well as V. Panetta et al., correspondingly protected amines must first be prepared. After the reaction has been completed, as also in the process of the Dow Chemical Company, Nycomed (WO 96/28433) and Schering (DE19608307), the cleavage of these protective groups is necessary as an additional reaction step, which produces a poorer material balance relative to the desired product. In the case of tetramerization of benzylaziridine, it is necessary to work with large amounts of carcinogenic substances.

A profitable process should use raw materials that are as reasonably priced, as environmentally safe and as easily accessible as possible. The reaction times should also be short and should occur with little energy use. Moreover, the amounts of material during the overall synthesis should be as small as possible.

This object is achieved by this invention. It has been found that a process for the production of cyclene characterized in that in a single-pot process, triethylenetetramine is reacted with 40% glyoxal at 20° C. to 80° C. in a polar, protic solvent, preferably methanol, ethanol, isopropanol, butanol, glycol, water or mixtures thereof, especially preferably ethanol, within 4 to 40 hours, preferably 15 to 20 hours; after the solvent has been removed, the intermediate tricyclic compound that is thus formed is alkylated to the two secondary amine-nitrogens with a 1,2-difunctionalized alkylating agent $X(CH_2)_2X$, in which X stands for a nucleofuge group, preferably with 1,2-dibromoethane, 1,2-dichloroethane, 1,2-ditosylethane, 1,2-dimetylethane or 1,2-dioodoethane, especially preferably with 1,2-dichloroethane in a polar aprotic solvent, preferably in N,N-dimethylformamide (DMF), N,N-dimethylacetamide (DMAC), N-methylpyrrolidone (NMP), tetramethyl urea, formamide or dimethylpropylene urea (DMPU), especially preferably in DMF, optionally in the presence of an auxiliary base, preferably sodium carbonate, potassium carbonate, calcium carbonate, sodium bicarbonate, potassium hydrogen carbonate, magnesium carbonate, magnesium hydrogen carbonate, lithium hydroxide or lithium carbonate, especially preferably without an auxiliary base, at 20 to 120° C., preferably 30 to 70° C., within 2 to 24 hours, preferably 6 to 10 hours; after the solvent has been removed, the thus obtained condensation product is treated with hydrazine hydrate in a polar protic solvent, preferably methanol, ethanol, isopropanol, butanol, glycol, water and/or mixtures thereof, especially preferably ethanol, at a pH of 3 to 6, preferably 3 to 4, 12 to 48 hours, preferably 25 to 35 hours, at reflux temperature; then the cyclene is released from the cyclene salt by adding a base, preferably sodium hydroxide, potassium hydroxide, calcium hydroxide or a basic ion exchanger, especially preferably sodium hydroxide and potassium hydroxide, and after the reaction solution is evaporated to the dry state, it is isolated, surprisingly enough achieves the above-mentioned object.

The isolation of the cyclene is preferably carried out by crystallization from toluene, trifluoromethylbenzene or diethoxymethane, whereby the latter is especially preferred.

By way of example, diagram 3 again sheds light on the process of the synthesis according to the invention:

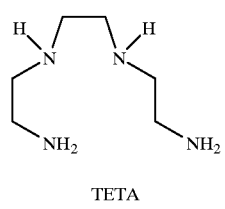

TETA

1) Glyoxal EtOH
   20° C. 20h
2) ClCH$_2$CH$_2$Cl/DMF
   40° C. 8h
3) H$_2$N—NH$_2$·H$_2$O
   pH 4/HCl
   Reflux 30h
4) KOH
   pH 13
5) DEM
   50–65% von TETA

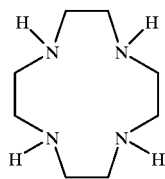

[Key:]
von=of

Advantages of the Process:

The process for the production of cyclene according to the invention has considerable advantages relative to the previous processes due to its design as a single-pot process.

- No time-intensive and raw material-intensive isolating steps of the intermediate products are necessary.
- The reaction with amine is carried out without generating considerable amounts of by-products.
- The raw materials are reasonably priced and easily accessible.
- Few wastes accumulate.
- The total synthesis time is short.
- A new, economical purification process for cyclene is used.
- The yield is higher than in the process of the prior art.

The following example is used for a more detailed explanation of the subject of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 198 56 481.3 filed Dec. 2, 1998, and U.S. Provisional Application No. 60/116,230 filed Jan. 15, 1999, are hereby incorporated by reference.

EXAMPLE 1

1.4.7.10 Tetraazacyclododecane (=cyclene):

50 g of triethylenetetramine (0.342 mol) is dissolved in 1 l of ethanol and mixed with 39 ml of 40% glyoxal in water (0.342 mol) at room temperature. After 20 hours of stirring, the solvent is distilled off in a vacuum, and an orange-colored oil, which is taken up in 400 ml of dimethylformamide and mixed with 81.2 ml (101.5 g=1.026 mol) of 1,2-dichloroethane, is obtained. After 8 hours of stirring at 40° C., it is concentrated by evaporation in a vacuum, the residue is taken up in 400 ml of ethanol and acidified to about pH=3–4 with 37% aqueous hydrochloric acid. 166 ml (171 g=3.42 mol) of hydrazine hydrate is added to this reaction solution at room temperature, and it is heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed. The residue is mixed with 25 g of activated carbon and 100 ml of formaldehyde diethylacetal, and it is heated under reflux for some time before the hot solution is filtered through a membrane. After the solution is cooled, the product is isolated by filtration. 38.3 g of cyclene (0.222 mol=65% of theory) is obtained as a crystalline solid.

EXAMPLE 2

1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethylformamide and mixed with 88.5 ml (192.8 g=1.026 mol) of 1,2-dibromoethane. After 6 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature, and it is heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal, and it is heated under reflux for some time before the hot solution is filtered through a membrane. After the solution is cooled, the product is isolated by filtration.

39.5 g of cyclene (67% of theory) is obtained as a crystalline solid.

EXAMPLE 3

1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which is then taken up in 400 ml of dimethylformamide and is mixed with 82.6 ml (274.8 g=1.026 mol) of 1,2-diiodoethane. After 5 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature, and it is heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal, and it is heated under reflux for some time before the hot solution is filtered through a membrane. After the solution is cooled, the product is isolated by filtration.

37.1 g of cyclene (63% of theory) is obtained as a crystalline solid.

EXAMPLE 4

1,4,7,10-Tetraazacyclododecane (=cyclene)

50 g of triethylenetetramine (0.342 mol) is dissolved in 1 ml of methanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethylformamide and mixed with 81.2 ml (101.5 g=1.026 mol) of 1,2-dichloroethane. After 8 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature, and it is heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal, and it is heated under reflux for some time before the hot solution is filtered through a membrane. After the solution is cooled, the product is isolated by filtration.

37.7 g of cyclene (64% of theory) is obtained as a crystalline solid.

EXAMPLE 5
1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethyl acetamide and is mixed with 81.2 ml (101.5 g=1.026 mol) of 1,2-dichloroethane. After 8 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature and heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal and heated under reflux for some time before the hot solution is filtered through a membrane. After the solution is cooled, the product is isolated by filtration. 37.7 g of cyclene (64% of theory) is obtained as a crystalline solid.

EXAMPLE 6
1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of tetramethylurea and mixed with 81.2 ml (101.5 g=1.026 mol) of 1,2-dichloroethane. After 8 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature and heated under reflux for 30 hours. The reaction solution is set at pH=13 with solid potassium hydroxide. The reaction solution is subsequently concentrated by evaporation in a vacuum, taken up once more in 100 ml of ethanol, and the solvent is again removed in a vacuum. The residue is mixed with 25 g of activated carbon and 150 ml of formaldehyde diethylacetal, and it is heated under reflux for some time before the hot solution is filtered through a membrane. After the solution is cooled, the product is isolated by filtration. 37.1 g of cyclene (63% of theory) is obtained as a crystalline solid.

EXAMPLE 7
1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of tetramethylurea and mixed with 88.5 ml (192.8 g=1.026 mol) of 1,2-dibromoethane. After 6 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution at room temperature and heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal and heated under reflux for some time before the hot solution is filtered through a membrane. After the solution is cooled, the product is isolated by filtration. 37.6 g of cyclene (64% measured) is obtained as a crystalline solid.

EXAMPLE 8
1,4,7,10-Tetraazacyclododecane (=cyclene)

50 g of triethylenetetramine (0.342 mol) is dissolved in 1 l of methanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethylformamide and mixed with 88.5 ml (192.8 g=1.026 mol) of 1,2-dibromoethane. After 6 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution and heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal and heated under reflux for some time before the hot solution is filtered through a membrane. After the solution is cooled, the product is isolated by filtration. 35.9 g of cyclene (61% of theory) is obtained as a crystalline solid.

EXAMPLE 9
1,4,7,10-Tetraazacyclododecane (=cyclene)

50 g of triethylenetetramine (0.342 mol) is dissolved in 1 l of ethanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethylformamide and mixed with 81.2 ml (101.5 g=1.026 mol) of 1,2-dichloroethane. After 8 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added at room temperature to this reaction solution, and then it is heated under reflux for 30 hours. The reaction solution is set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 200 ml of toluene and heated under reflux for some time before the hot solution is filtered through a membrane. After the solution is cooled, the product is isolated by filtration. 35.8 g of cyclene (61% of theory) is obtained as a crystalline solid.

EXAMPLE 10

1,4,7,10-Tetraazacyclododecane (=cyclene)

50 g of triethylenetetramine (0.342 mol) is dissolved in 1 l of 2-propanol and mixed at room temperature with 39 ml of 40% glyoxal in water (0.342 mol). After 20 hours of stirring, the solvent is distilled off in a vacuum, and an orange-colored oil is obtained, which then is taken up in 400 ml of dimethylformamide and mixed with 81.2 ml (101.5 g=1.026 mol) of 1,2-dichloroethane. After 8 hours of stirring at 40° C., it is concentrated by evaporation in a vacuum, the residue is taken up in 400 ml of ethanol and acidified to pH=3–4 with 37% aqueous hydrochloric acid. 166 ml (171 g=3.42 mol) of hydrazine hydrate is added to this reaction solution and heated under reflux for 30 hours. The reaction solution is then set at pH=13 with solid potassium hydroxide. The reaction solution is subsequently concentrated by evaporation in a vacuum, taken up once more in 100 ml of ethanol, and the solvent is removed again in a vacuum. The residue is mixed with 25 g of activated carbon and 150 ml of formaldehyde diethylacetal and heated under reflux for some time before the hot solution is filtered through a membrane. After the solution is cooled, the product is isolated by filtration. 37.2 g of cyclene (63% of theory) is obtained as a crystalline solid.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Process for the production of cyclene

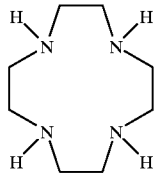

characterized in that in a single-pot process, triethylenetetramine is reacted with 40% glyoxal at 20 C. to 80° C. in a polar, protic solvent within 4 to 40 hours; after the solvent has been removed, the intermediate tricyclic compound that is thus formed is alkylated to the two secondary amine-nitrogens with a 1,2-difunctionalized alkylating agent $X(CH_2)_2X$, in which X stands for a nucleofuge group, in a polar aprotic solvent, optionally in the presence of an auxiliary base, at 20 to 120° C. within 2 to 24 hours; after the solvent has been removed, the thus obtained condensation product is treated with hydrazine hydrate in a polar protic solvent at a pH of 3 to 6 within 12 to 48 hours at reflux temperature; then the cyclene is released from the cyclene salt by adding a base, and after the reaction solution is evaporated to the dry state, it is isolated.

2. Process according to claim 1, wherein methanol, ethanol, isopropanol, butanol, glycol, water or mixtures thereof are used as polar protic solvents.

3. Process according to claim 1, wherein N,N-dimethylformamide (DMF), N,N-dimethylacetamide (DMAC), N-methylpyrrolidone (NMP), tetramethylurea, formamide or dimethylpropylene urea (DMPU) is used as a polar aprotic solvent.

4. Process according to claim 1, wherein 1,2-dibromoethane, 1,2-dichloroethane, 1,2-ditosylethane, 1,2-dimesylethane or 1,2-diiodoethane is used as an alkylating agent $X(CH_2)_2X$.

5. Process according to claim 1, wherein sodium carbonate, potassium carbonate, calcium carbonate, sodium bicarbonate, potassium hydrogen carbonate, magnesium carbonate, magnesium hydrogen carbonate, lithium hydroxide or lithium carbonate is used as an auxiliary base that is optionally used in the condensation reaction with the 1,2-difunctionalized alkylating agent $X(CH_2)_2X$.

6. Process according to claim 1, wherein sodium hydroxide, potassium hydroxide, calcium hydroxide or a basic ion exchanger is used as a base to release cyclene.

7. Process according to claim 1, wherein the reaction of triethylenetetramine is performed with glyoxal at 20 to 40° C. within 15 to 20 hours.

8. Process according to claim 1, wherein the condensation reaction is performed with the 1,2-difunctionalized alkylating agent $X(CH_2)_2X$ at 30 to 70° C. and within 6 to 10 hours.

9. Process according to claim 1, wherein the reaction of the condensation product with an amine is performed within 25 to 35 hours.

10. Process according to claim 1, wherein the reaction product is isolated by treating with toluene, trifluoromethylbenzene or diethoxymethane the residue that is obtained after the reaction solution has been concentrated by evaporation.

11. Process according to claim 1, wherein the reaction product is mixed with activated carbon and isolated by treating with formaldehyde diethylacetal the residue that is obtained after the reaction solution has been concentrated by evaporation.

12. Process according to claim 1, wherein ethanol is the polar protic solvent.

13. Process according to claim 1, wherein N,N-dimethylformamide (DMF) is the polar aprotic solvent.

14. Process according to claim 1, wherein 1,2-dichloroethane is the alkylating agent $X(CH_2)_2X$.

15. Process according to claim 1, wherein the condensation reaction is performed with the 1,2-difunctionalized alkylating agent $X(CH_2)_2X$ within 2 to 24 hours.

16. Process according to claim 1, wherein the obtained condensation product is treated with hydrazine hydrate in the polar protic solvent at a pH of 3 to 6.

17. Process according to claim 1, wherein the obtained condensation product is treated with hydrazine hydrate in the polar protic solvent at a pH of 3 to 4.

18. Process according to claim 1, wherein sodium hydroxide or potassium hydroxide is used as a base to release cyclene.

19. Process according to claim 1, wherein ethanol is the polar protic solvent, N,N-dimethylformamide (DMF) is the polar aprotic solvent, 1,2-dichloroethane is the alkylating agent $X(CH_2)_2X$, and sodium hydroxide or potassium hydroxide is used as a base to release cyclene; and the reaction of triethylenetetramine with glyoxal is performed at 20 to 40° C. within 15 to 20 hours.

* * * * *

UNITED STATES PATENT AND TRADEMARK OFFICE
CERTIFICATE OF CORRECTION

PATENT NO.    : 6,156,890
DATED         : December 5, 2000
INVENTOR(S)   : Platzek et al.

It is certified that error appears in the above-identified patent and that said Letters Patent is hereby corrected as shown below:

Column 9,
Line 46, reads "at 20 C to 80ºC." please amend it to read -- at 20ºC to 80ºC. --

Signed and Sealed this

Fifteenth Day of April, 2003

JAMES E. ROGAN
*Director of the United States Patent and Trademark Office*